United States Patent
Barnette et al.

(12) 
(10) Patent No.: US 6,461,481 B1
(45) Date of Patent: Oct. 8, 2002

(54) PROCESS FOR REMOVING WATER FROM ORGANOBORANE COMPOUNDS

(75) Inventors: Willie Jon Barnette, Orange, TX (US); Bruce Edwin Murphree, Beaumont, TX (US); John Joseph Ostermaier, Wilmington, DE (US)

(73) Assignee: E. I. du Pont de Nemours and Company, Wilmingotn, DE (US)

( * ) Notice: Subject to any disclaimer, the term of this patent is extended or adjusted under 35 U.S.C. 154(b) by 0 days.

(21) Appl. No.: 09/651,943

(22) Filed: Aug. 31, 2000

(51) Int. Cl.$^7$ .............. B01D 3/34; C02F 5/02; C01B 35/00
(52) U.S. Cl. .............. 203/14; 34/378; 34/427; 202/204; 202/176; 203/39; 203/60; 203/68; 203/69; 203/70; 203/98; 210/804; 210/805; 210/806; 568/1; 423/276

(58) Field of Search .............. 203/14, 98, 39, 203/60, 100, 68, 69, 70; 568/1; 558/87; 202/158, 204, 176; 210/766, 770, 804, 805, 800, 806; 34/378, 427; 423/276, 278

(56) References Cited

U.S. PATENT DOCUMENTS

| | | | | |
|---|---|---|---|---|
| 3,496,218 A | * | 2/1970 | Drinkard, Jr. .............. | 558/338 |
| 4,045,495 A | * | 8/1977 | Nazarenko et al. .............. | 568/1 |
| 5,545,743 A | * | 8/1996 | Cannady et al. .............. | 203/6 |

* cited by examiner

*Primary Examiner*—Virginia Manoharan

(57) ABSTRACT

A method of removing water from wet organoborane by dissolving the wet organoborane in an organic solvent in which water is incompletely soluble, decanting any insoluble water, and distilling the organic phase to remove water which may be contained therein.

8 Claims, 2 Drawing Sheets

PROCESS FOR REMOVING WATER FROM ORGANOBORANE COMPOUNDS

FIELD OF THE INVENTION

The present invention concerns a process for drying wet organoborane compounds.

BACKGROUND OF THE INVENTION

Certain organoborane compounds (boron hydride compounds in which hydrogen is substituted with organic moieties) are known to be useful as promoters in hydrocyanation reactions. A commercially important hydrocyanation reaction that utilizes these promoters is the conversion of pentenenitrile compounds to adiponitrile. For example, U.S. Pat. No. 3,496,218 describes a process for hydrocyanation of non-conjugated ethylenically unsaturated organic compounds, such as 3-pentenenitrile, in the presence of a nickel/triarylphosphite catalyst and a triorganoborane compound promoter, such as triphenylborane, to produce adiponitrile. Adiponitrile is an intermediate in the production of hexamethylene diamine, a nylon-6,6 component. Adiponitrile is also an intermediate in the production of caprolactam and nylon-6.

Organoborane compounds are easily hydrolyzed. For example, triphenylborane can be hydrolyzed to diphenylborinic and phenylboronic acids in the presence of water. Even at low temperatures (for example, below 10° C.), triphenylborane will slowly hydrolyze to diphenylborinic and phenylboronic acids with trace amounts (e.g. 10 ppm) of water present. At elevated temperatures, the hydrolysis rate significantly increases. It is important to dry organoborane compounds which are used as promoters in hydrocyanation reactions, because many hydrocyanation reactions occur at elevated temperatures. Current drying methods include exposure of organoborane compounds to hot nitrogen and molecular sieves. Use of hot nitrogen leads to degradation of some organoborane to undersirable organoborinic and boronic acids. As a result, there is a need in the art for an improved method of drying organoborane compounds that minimizes the production of such undesirable degradation products.

BRIEF DESCRIPTION OF THE DRAWING

The Drawing consists of two figures in which like reference numerals are used to indicate like elements.

BRIEF SUMMARY OF THE INVENTION

Figure 1:
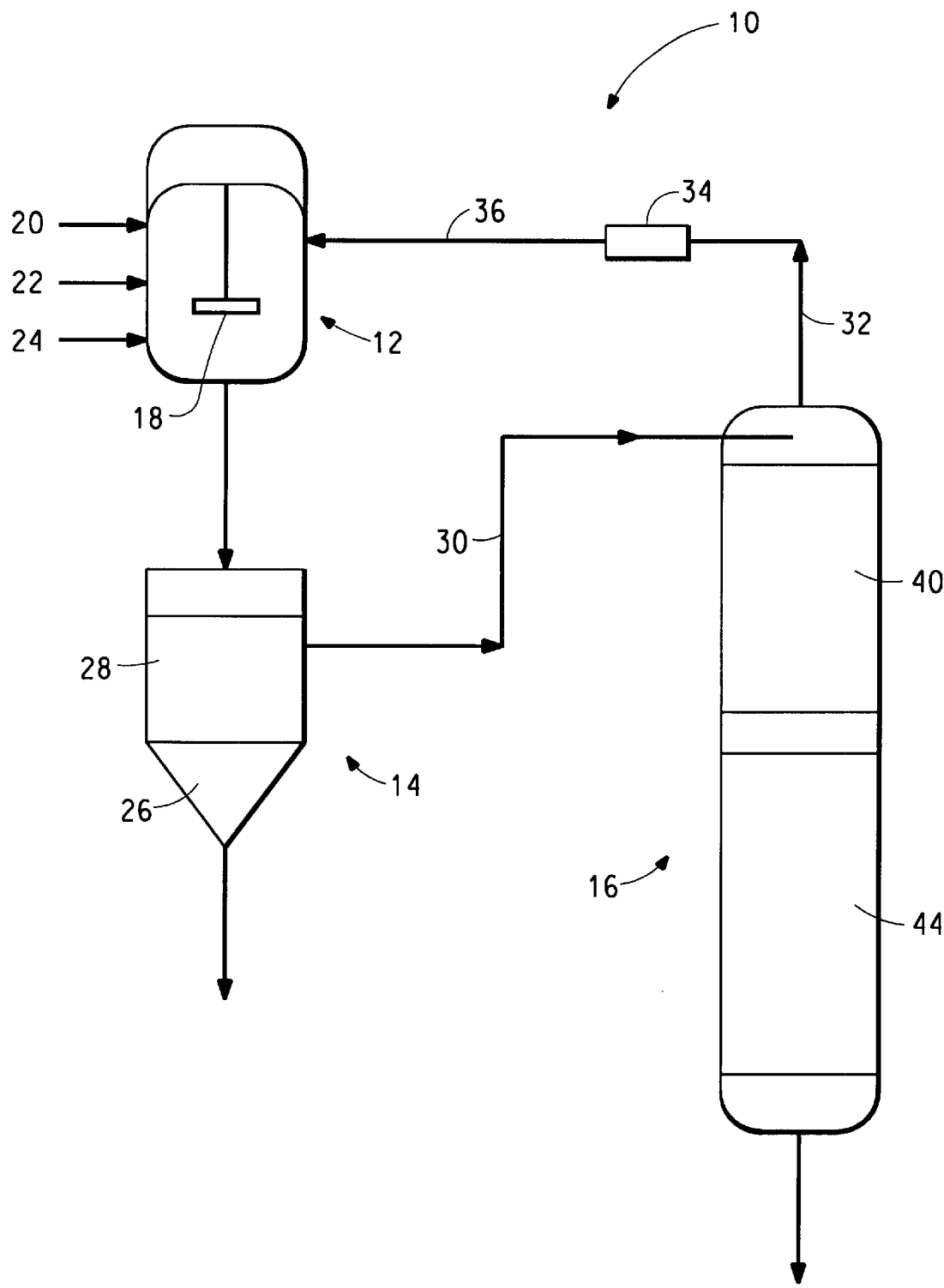
FIG. 1 depicts apparatus for carrying out the method of the present invention.

The present invention is a method of removing water from a wet organoborane compound, comprising:
(a) forming a mixture by mixing the wet organoborane compound with a solvent in which water is incompletely soluble and which solvent comprises a nitrile compound;
(b) allowing the mixture of step (a) to separate into an aqueous phase and an organic phase, which organic phase comprises substantially all of the organoborane compound;
(c) separating the aqueous phase from the organic phase; and
(d) distilling the organic phase to remove water which may be contained therein.

DETAILED DESCRIPTION OF THE INVENTION

The present invention concerns a method of removing water from wet organoborane compound. The expression "wet organoborane compound" means an organoborane compound which is associated with water. Typical wet organoborane compounds can be associated with 5% to 25% water by weight. Preferred organoborane compounds are triphenylborane, tri(paratolyl)borane, tri(metatolyl)borane, tri(orthotolyl)borane, tri(biphenyl)borane, tri(paramethoxyphenyl)borane, tri(parachlorophenyl)borane, tri(paraflorophenyl)borane, phenylboroxin, diphenyl (phenoxy)borane, and phenyl(diphenoxy)borane. An especially preferred organoborane is triphenylborane.

The wet organoborane compound is dissolved in a solvent comprising a nitrile compound to produce an organoborane solution. Preferably, the solvent should have a boiling point of 20 to 200 C. The solvent should be one that has low water solubility. Preferred nitrile compounds include 3-pentenenitrile, 4-pentenenitrile, and 2-pentenenitrile. A mixture of two or more of the pentenenitrile compounds may be used. These mixtures are referred to herein as "pentenenitriles," "pentenenitrile mixtures" or "mixtures of pentenenitriles." Other nitriles, such as methyl butenenitriles, butenenitriles, pentanenitriles, methyl butanenitriles, butanenitriles, and acetonitrile, also may be used. This solvent may also contain additional compounds that are miscible with the nitrile compound. These additional compounds serve as co-solvents. Preferred co-solvents are cycloheptane, cyclohexane, methylcylopentane, cyclopentane, heptane, hexane, pentane, toulene, and benzene.

An especially preferred co-solvent is cyclohexane. In the present invention, an especially preferred solvent comprises a mixture of pentenenitriles (including 3-pentenenitrile) and cyclohexane. Preferably, the ratio of cyclohexane to pentenenitrile is 0 to 10 by weight. A preferred ratio of cyclohexane to pentenenitrile is 2 to 5 by weight. In order to reduce hydrolysis of the organoborane compound before decantation and distillation, the solution may be maintained at a reduced temperature, preferably between 0 to 20° C. The weight percent of the organoborane compound in solvent is not critical and typically ranges from 1 to 10%

Water that is not miscible in the organoborane solution is decanted. Any residual water in the remaining organoborane solution is then removed by distillation.

By decanting most of the water prior to distillation, hydrolysis of the organoborane compound during distillation is minimized.

Referring now to FIG. 1, there is shown apparatus 10 that can be used for carrying out the present method. The apparatus 10 comprises a dissolving tank 12, a decanting tank 14, and a distillation column 16. Dissolving tank 12 contains a stirrer 18.

Wet organoborane compound crystals 20, solvent 22, and optional co-solvent 24 are fed to dissolving tank 12, in which the crystals are dissolved by means of stirrer 18. In the case of triphenylborane, the solvent preferably is a mixture of pentenenitriles, and the co-solvent is preferably cyclohexane. Preferably the contents of dissolving tank 12 are kept at low temperatures, such as 10 to 15 C.

Figure 2:
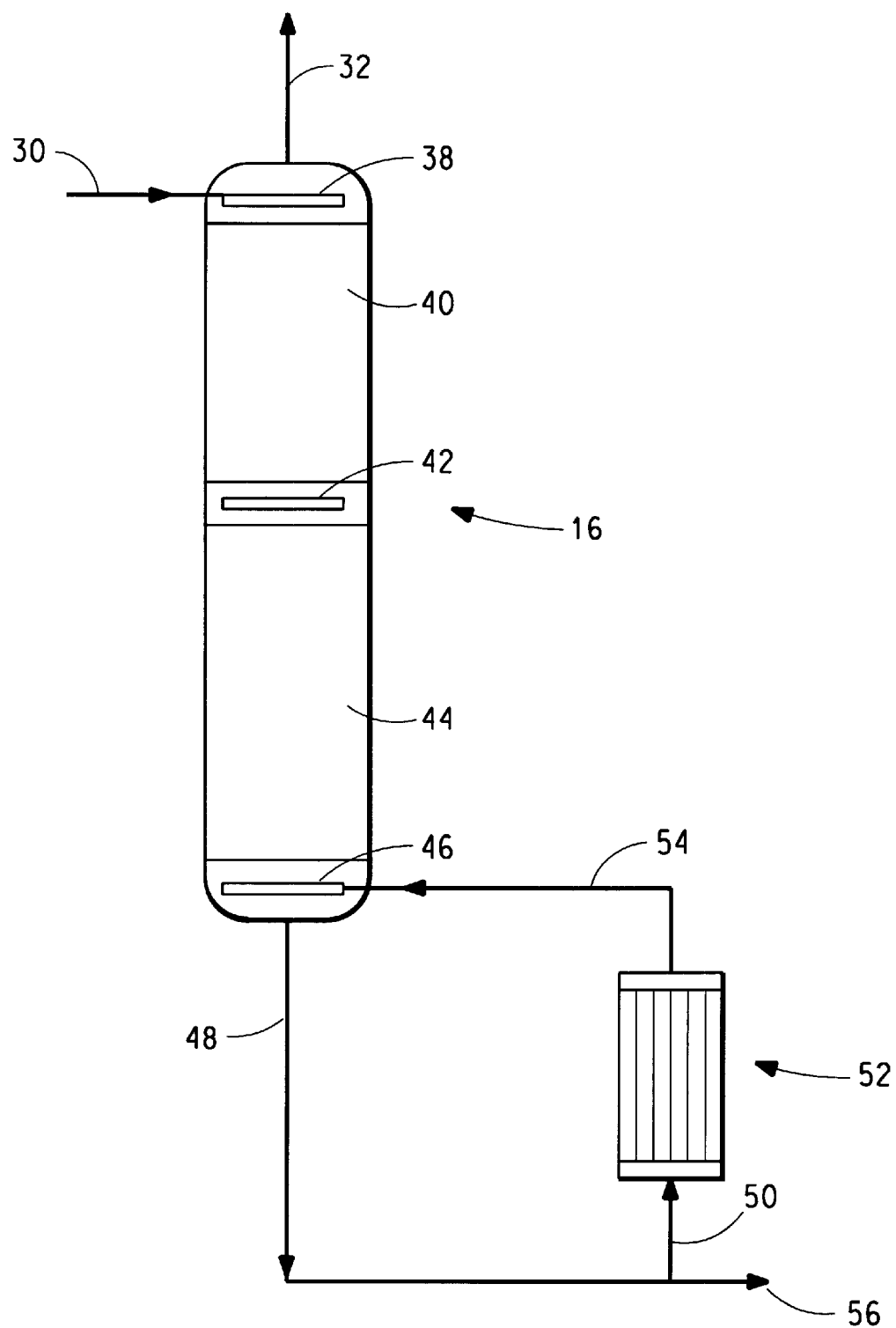
FIG. 2 depicts a distillation column for carrying out the method of the present invention.

The contents of dissolving tank 12 are then fed to decanting tank 14, where the contents are allowed to separate into an aqueous phase 26 (containing most of the water present in the dissolving tank 12), and an organic phase 28. The organic phase 28 contains substantially all the organoborane compound dissolved in the organic solvent and co-solvent, and a minor portion of the water initially present in the contents of dissolving tank 12. The aqueous phase 26 is decanted and treated as waste material. The organic phase 28 is fed as a stream 30 to the top portion of distillation column 16. In distillation column 16, water and most of the co-solvent are vaporized and removed as overhead stream 32, which is condensed in condenser 34 to produce a recycle stream 36, which is fed into dissolving tank 12. Organoborane compound and solvent are removed from the bottom of distillation column 16. Referring now to FIG. 2, distillation column 16 is shown in greater detail. The function of distillation column 16 is to remove the final traces of water from the organoborane and to concentrate it in the product. Water and cyclohexane are removed overhead in stream 32. The organic phase 30 is introduced into the top portion of column 16 in which a feed distributor 38 causes the organic phase 30 to disperse across the cross-section of the column 16. The column 16 is divided into two broad zones. An upper zone 40 contains a random packing material, such as Norton 15 IMTP high efficiency packing rings. A lower zone 44 contains a structured packing material, such as Norton HS-10 ISP. Dividing the two zones is a liquid collector and redistributor 42. Below the lower zone 44 is a vapor distributor 46. The column 16 is heated at its bottom portion by the output of a reboiler, which, itself, is heated by steam. A stream 48 containing organoborane compound and solvent is withdrawn from the bottom of column 16. A portion 50 of stream 48 is fed to a reboiler 52 in which the contents of stream 50 are partially vaporized and returned to the lower portion of column 16 below vapor distributor 46. The desired product is recovered as stream 56, which contains the organoborane compound, substantially free of water, dissolved in the solvent.

In a preferred mode, wherein the organoborane is triphenylborane, the dissolving tank 12 is operated as follows. Sufficient solvent, (preferably pentenenitriles) is added to the dissolving tank 12, such that after the triphenylborane solution is dried in the distillation column 16, the concentration of triphenylborane is about 25 wt %. The pentenenitriles concentration is about 70 wt %, with the remainder being primarily co-solvent (cyclohexane). The pentenenitriles concentration in the distillation column stream 56 is such that the triphenylborane remains in solution at ambient temperature. The cyclohexane to pentenenitriles weight ratio in the dissolving tank is about 80/20. Preferably, the contents of dissolving tank 12 are kept at 15 C., which minimizes the hydrolytic degradation of triphenylborane.

In a preferred mode, wherein the organoborane is triphenylborane, the decanting tank 14 is operated as follows. The temperature should be kept low, preferably about 15 C. to prevent hydrolytic degradation of the triphenylborane. In the decantation step, the cyclohexane (a low water solubility co-solvent) serves to drive most of the water into the decanted aqueous stream and minimize water fed to the distillation column 16. Cyclohexane also minimizes the loss of organics (cyclohexane, pentenenitrile, and triphenylborane) to the stream 30. Other co-solvents, such as benzene, hexane, and other low water solubility solvents, should work similarly to cyclohexane. The ratio of recycle stream 36 to pentenenitrile feed stream 22 may vary over a wide range. An 80/20 ratio is preferred.

In a preferred mode, wherein the organoborane is triphenylborane, the distillation column 16 is operated as follows. Overhead stream 32 has about 5wt % pentenenitrile, with the balance being cyclohexane and water. Preferably, the distillation column 16 is operated at 2 psig, but can be operated at lower pressures if so desired. The 2 psig value minimizes column temperatures and maintains positive pressure operation to prevent air leaks into the process. The temperature at the top of distillation column 16 preferably is about 85–86 C., and the temperature of the bottom of the column is about 128–129 C. The reboiler exit temperature is 142–143 C. The temperature profiles in each of zones 40, 44 is virtually constant. The temperature of upper zone 40 is 85–86 C., and the temperature of lower zone 44 is 86 to 87 C. The useful temperature range in the distillation column 16 depends on the residence time in the upper zone 40. Packed columns are especially preferred, because they combine short liquid residence times with proper vapor-liquid contact necessary for distillation. Use of multiple zones of packing versus a single zone of packing is not critical as long as short liquid residence time and proper vapor-liquid contact for distillation staging is maintained. Use of random packing versus structured packing is also not critical, as long as the residence time for the liquid in the upper zone 40 is short. Random packing is preferred for the upper zone 40, so that if the decanting is incomplete and any residual two-phase liquid (aqueous/organic) feed reaches the column, the random packing in the upper zone 40 will minimize the possibility of free water falling down to the base of the column, where it could cause hydrolytic degradation of the triphenylborane.

The stream 30 is distributed across the top of the upper zone 40 through the distributor 38. For packed columns, it is essential for good vapor-liquid contact that liquid be distributed evenly over the packing. The liquid then travels down the upper zone 40 of distillation column 16 through random packing. A suitable packing is Norton 15 IMTP high efficiency packing rings. (Norton Chemical Process Products Corporation, P.O. Box 350, Akron, Ohio. 44309–0350) The liquid then is redistributed by liquid collector and redistributor 42, located below the random packing, before entering the lower zone 44 which contains structured packing (Norton HS-10 ISP).

A thermal siphon reboiler using 175 psig steam is used to boil-up the stream 50 in the base of distillation column 16. Vapor from the reboiler is distributed evenly across the bottom of the structured packing section using vapor distributor 46. Varying the steam flow controls the temperature of stream 54.

Experiments were conducted to compare the effectiveness of the present method with that of the prior art molecular sieves/hot nitrogen technology for their respective abilities to dry wet triphenylborane. The resulting dried products were compared for water content (ppm) and mole ratio of diphenylborinic acid to triphenylborane. The results are indicated in the table below and show that the product of the present invention was drier and contained less degradation product than that of the prior art method.

| Method | Mole Ratio | H$_2$O (ppm) |
| --- | --- | --- |
| Present Method | 0.011 | 156 |
| Prior Art | 0.032 | 338 |

What is claimed:
1. A method of removing water from a wet organoborane compound, comprising:
 (a) forming a mixture by mixing the wet organoborane compound with a solvent in which water is incom- pletely soluble and which solvent comprises at least one nitrile compound;

(b) allowing the mixture of step (a) to separate into an aqueous phase and an organic phase, which organic phase comprises substantially all of the organoborane compound;

(c) separating the aqueous phase from the organic phase; and (d) distilling the organic phase to remove water which may be contained therein.

2. The method of claim 1 wherein the distilling step (d) is performed by introducing the mixture into the upper zone of a distillation column comprising an upper zone and a lower zone; removing a major portion of water contained in said mixture from the column as an overhead and removing the organoborane compound from the lower zone of the column.

3. The method of claim 2 wherein the solvent further comprises at least one co-solvent selected from the group consisting of cyclohexane, hexane, and benzene.

4. The method of claim 3 wherein the organoborane compound is triphenylborane.

5. The method of claim 4 wherein the nitrile compound is 2-, 3-, or 4-pentenenitrile.

6. The method of claim 5 wherein the co-solvent is cyclohexane.

7. The method of claim 5 wherein the cosolvent is cyclohexane and the nitrile compound is 3-pentenenitrile.

8. The method of claim 7 wherein the upper zone of the column comprises random packing and the lower zone of the column comprises structured packing.

* * * * *